(12) United States Patent
Kitamura et al.

(10) Patent No.: US 6,866,998 B1
(45) Date of Patent: Mar. 15, 2005

(54) CELLULAR ASSAYS FOR IDENTIFYING SIGNALING PEPTIDES

(75) Inventors: Toshio Kitamura, 6-16-20-406, Shirokane, Minato-ku Tokyo 108-0072 (JP); Tetsuo Kojima, Niihari-mura (JP)

(73) Assignees: Chugai Seiyaku Kabushiki Kaisha, Tokyo (JP); Toshio Kitamura, Tokyo (JP)

( * ) Notice: Subject to any disclaimer, the term of this patent is extended or adjusted under 35 U.S.C. 154(b) by 0 days.

(21) Appl. No.: 09/555,165

(22) PCT Filed: Nov. 26, 1998

(86) PCT No.: PCT/JP98/05326

§ 371 (c)(1),
(2), (4) Date: Aug. 22, 2000

(87) PCT Pub. No.: WO99/26978

PCT Pub. Date: Jun. 3, 1999

(30) Foreign Application Priority Data

Nov. 26, 1997 (JP) ............................................. 9/324912

(51) Int. Cl.[7] ........................... C12Q 1/68; C12P 21/06; C12P 21/04
(52) U.S. Cl. ......................... 435/6; 435/69.1; 435/69.8; 435/69.7; 435/70.1; 435/320.1; 435/325; 536/23.5; 536/24.1
(58) Field of Search ........................ 435/6, 69.1, 69.8, 435/70.1, 70.3, 173.3, 91.4, 320.1, 69.7, 325; 536/23.5, 24.1

(56) References Cited

U.S. PATENT DOCUMENTS 5,536,637 A * 7/1996 Jacobs ............................ 435/6
5,675,062 A * 10/1997 Haber et al. ................. 424/569

FOREIGN PATENT DOCUMENTS

| EP | 0 939 119 A1 | 7/1997 |
| JP | 0 607 054 A | 2/1999 |
| JP | 11 32779 | 2/1999 |
| WO | WO 96/40904 | 12/1996 |

OTHER PUBLICATIONS

Ngo et al., 1994, The Protein Folding Problem and Tertiary Structure Prediction, pp. 492–495.*
Wells, Aditivity of Mutational Effects in Proteins, 1990, Biochemistry, vol. 29, No: 37, pp. 8509–8517.*
Livnah et al. Functional mimicry of a protein hormone by a peptide agonist: The EPO receptor complex at 2.8 A (1996), Scienc vol. 273, pp 464–471.*
Shirozu et al., Characterization of Novel Secreted and Membrane Proteins Isolated by the Signal Sequence Trap Method. (1996), Genomics 37, pp 273–280.*
Kristoffersen et al., Signal Sequence Trap to Clone cDNAs Encoding Secreted or Membrane–Associated Plant Proteins. (1996), Analytical Biochemistry 243, 127–132.*
Hayashida et al., "Molecular cloning of a second subunit of the receptor for human granulocyte–macrophage colony–stimulating factor (GM–CSF): Reconstitution of a high–affinity GM–CSF receptor", *Proc. Natl. Acad. Sci. USA* 87:9655–9659 (1990).
Onishi et al., "Identification of an Oncogenic Form of the Thrombopoietin Receptor MPL Uing Retrovirus–Mediated Gene Transfer", *Blood* 88:1399–1406 (1996).
Vigon et al., "Molecular cloning and characterization of MPL, the human homolog of the v–mpl oncogene: Identification of a member of the hematopoietic growth factor receptor superfamily", *Pro. Natl. Acad. Sci. USA* 89:5640–5644 (1992).
Klein et al. "Selection for genes . . . ," Proc. Natl. Acad. Sci. USA, 93:7108–7113, 1996.
Tashiro et al., "Signal Sequence . . . ," Science, 261:600–643, 1993.
Kitamura et al., "Efficient screening . . . ," Proc. Natl. Acad. Sci. USA, 92:9146–9150, 1995.
Pear et al., "Production of . . . ," Proc. Natl. Acad. Sci. USA, 90:8392–8396, 1993.
Onishi et al., "Applications of . . . ," Experimental Hematology, 24:324–329, 1996.
Jacobs et al., "A genetic . . . ," Gene, 198:289–296, 1997.

* cited by examiner

*Primary Examiner*—Brenda Brumback
*Assistant Examiner*—Jegatheesan Seharaseyon
(74) *Attorney, Agent, or Firm*—Fish & Richardson P.C.

(57) ABSTRACT

The invention includes a DNA encoding a known translocatable protein, for example, human mpl, lacking secretory ability due to deletion of its secretory signal and the major part of the extracellular region thereof. This DNA is present in an expression vector into which a test cDNA from a cDNA library is ligated. The expression vector containing the known DNA and the test cDNA expresses a chimeric protein encoded by these two nucleic acid molecules. Cells expressing the newly constructed vector are capable of proliferating if the test cDNA is a secretory protein. Thus, cDNAs encoding secretory proteins including type I membrane proteins and type II membrane proteins can be detected and isolated by constructing a cDNA library and screening it for ability to promote cell proliferation.

30 Claims, 1 Drawing Sheet

SEQUENCE LISTING

<160> NUMBER OF SEQ ID NOS: 15

<210> SEQ ID NO 1
<211> LENGTH: 43
<212> TYPE: DNA
<213> ORGANISM: Artificial Sequence
<220> FEATURE:
<223> OTHER INFORMATION: Artificially synthesized primer sequence

<400> SEQUENCE: 1
tgcggccgcc ctggagctgc gcccgcgatc ctgctaccgt tta      43

<210> SEQ ID NO 2
<211> LENGTH: 29
<212> TYPE: DNA
<213> ORGANISM: Artificial Sequence
<220> FEATURE:
<223> OTHER INFORMATION: Artificially synthesized primer sequence

<400> SEQUENCE: 2
gtatgtcgac tcaaggctgc tgccaatag      29

<210> SEQ ID NO 3
<211> LENGTH: 579
<212> TYPE: DNA
<213> ORGANISM: Artificial Sequence
<220> FEATURE:
<223> OTHER INFORMATION: Artificially manipulated human mpl sequence
<220> FEATURE:
<221> NAME/KEY: CDS
<222> LOCATION: (1)...(570)

<400> SEQUENCE: 3

```
gcg gcc gcc ctg gag ctg cgc ccg cga tct cgc tac cgt tta cag ctg      48
Ala Ala Ala Leu Glu Leu Arg Pro Arg Ser Arg Tyr Arg Leu Gln Leu
 1               5                  10                  15 cgc gcc agg ctc aac ggc ccc acc tac caa ggt ccc tgg agc tcg tgg      96
Arg Ala Arg Leu Asn Gly Pro Thr Tyr Gln Gly Pro Trp Ser Ser Trp
             20                  25                  30 tcg gac cca act agg gtg gag acc gcc acc gag acc gcc tgg atc tcc     144
Ser Asp Pro Thr Arg Val Glu Thr Ala Thr Glu Thr Ala Trp Ile Ser
         35                  40                  45 ttg gtg acc gct ctg cat cta gtg ctg ggc ctc aac gcc gtc ctg ggc     192
Leu Val Thr Ala Leu His Leu Val Leu Gly Leu Asn Ala Val Leu Gly
     50                  55                  60 ctg ctg ctg ctg agg tgg cag ttt cct gca cac tac agg aga ctg agg     240
Leu Leu Leu Leu Arg Trp Gln Phe Pro Ala His Tyr Arg Arg Leu Arg
 65                  70                  75                  80 cat gcc ctg tgg ccc tca ctt cca gac ctg cac cgg gtc cta ggc cag     288
His Ala Leu Trp Pro Ser Leu Pro Asp Leu His Arg Val Leu Gly Gln
                 85                  90                  95 tac ctt agg gac act gca gcc ctg agc ccg ccc aag gcc aca gtc tca     336
Tyr Leu Arg Asp Thr Ala Ala Leu Ser Pro Pro Lys Ala Thr Val Ser
            100                 105                 110 gat acc tgt gaa gaa gtg gaa ccc agc ctc ctt gaa atc ctc ccc aag     384
Asp Thr Cys Glu Glu Val Glu Pro Ser Leu Leu Glu Ile Leu Pro Lys
        115                 120                 125 tcc tca gag agg act cct ttg ccc ctg tgt tcc tcc cag gcc cag atg     432
Ser Ser Glu Arg Thr Pro Leu Pro Leu Cys Ser Ser Gln Ala Gln Met
    130                 135                 140 gac tac cga aga ttg cag cct tct tgc ctg ggg acc atg ccc ctg tct     480
Asp Tyr Arg Arg Leu Gln Pro Ser Cys Leu Gly Thr Met Pro Leu Ser
145                 150                 155                 160 gtg tgc cca ccc atg gct gag tca ggg tcc tgc tgt acc acc cac att     528
Val Cys Pro Pro Met Ala Glu Ser Gly Ser Cys Cys Thr Thr His Ile
                165                 170                 175 gcc aac cat tcc tac cta cca cta agc tat tgg cag cag cct tga         573
Ala Asn His Ser Tyr Leu Pro Leu Ser Tyr Trp Gln Gln Pro
            180                 185                 190 gtcgac                                                               579
```

<210> SEQ ID NO 4
<211> LENGTH: 190
<212> TYPE: PRT
<213> ORGANISM: Artificial Sequence
<220> FEATURE:
<223> OTHER INFORMATION: Artificially manipulated human mpl sequence

<400> SEQUENCE: 4

```
Ala Ala Ala Leu Glu Leu Arg Pro Arg Ser Arg Tyr Arg Leu Gln Leu
 1               5                  10                  15

Arg Ala Arg Leu Asn Gly Pro Thr Tyr Gln Gly Pro Trp Ser Ser Trp
             20                  25                  30
```

```
Ser Asp Pro Thr Arg Val Glu Thr Ala Thr Glu Thr Ala Trp Ile Ser
         35                  40                  45

Leu Val Thr Ala Leu His Leu Val Leu Gly Leu Asn Ala Val Leu Gly
 50                  55                  60

Leu Leu Leu Leu Arg Trp Gln Phe Pro Ala His Tyr Arg Arg Leu Arg
 65                  70                  75                  80

His Ala Leu Trp Pro Ser Leu Pro Asp Leu His Arg Val Leu Gly Gln
                 85                  90                  95

Tyr Leu Arg Asp Thr Ala Ala Leu Ser Pro Pro Lys Ala Thr Val Ser
                100                 105                 110

Asp Thr Cys Glu Glu Val Glu Pro Ser Leu Leu Glu Ile Leu Pro Lys
                115                 120                 125

Ser Ser Glu Arg Thr Pro Leu Pro Leu Cys Ser Ser Gln Ala Gln Met
130                 135                 140

Asp Tyr Arg Arg Leu Gln Pro Ser Cys Leu Gly Thr Met Pro Leu Ser
145                 150                 155                 160

Val Cys Pro Pro Met Ala Glu Ser Gly Ser Cys Cys Thr Thr His Ile
                165                 170                 175

Ala Asn His Ser Tyr Leu Pro Leu Ser Tyr Trp Gln Gln Pro
                180                 185                 190

<210> SEQ ID NO 5
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 5
cgaattcaaa gttctctgga ggatg                                          25

<210> SEQ ID NO 6
<211> LENGTH: 37
<212> TYPE: DNA
<213> ORGANISM: Artificial Sequence
<220> FEATURE:
<223> OTHER INFORMATION: Artificially synthesized primer sequence

<400> SEQUENCE: 6
cgaattcgcc gccaccatgg cacccgcccg ctcgccc                             37

<210> SEQ ID NO 7
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 7
agcggccgcc tcctggactg gctccca                                        27

<210> SEQ ID NO 8
<211> LENGTH: 1032
<212> TYPE: DNA
<213> ORGANISM: Artificial Sequence
<220> FEATURE:
<223> OTHER INFORMATION: Artificially synthesized human GM-CSF-human mpl
      fusion gene sequence
<220> FEATURE:
<221> NAME/KEY: sig_peptide
<222> LOCATION: (22)...(72)
<220> FEATURE:
<221> NAME/KEY: CDS
```

-continued

<222> LOCATION: (22)...(1023)

<400> SEQUENCE: 8

| | | | | | | | | | | |
|---|---|---|---|---|---|---|---|---|---|---|
| gaattcaaag ttctctggag g atg tgg ctg cag agc ctg ctg ctc ttg ggc | | | | | | | | | | 51 |
| | Met Trp Leu Gln Ser Leu Leu Leu Leu Gly | | | | | | | | | |
| | -15 | | | | | -10 | | | | |

| act gtg gcc tgc agc atc tct gca ccc gcc cgc tcg ccc agc ccc agc | 99 |
|---|---|
| Thr Val Ala Cys Ser Ile Ser Ala Pro Ala Arg Ser Pro Ser Pro Ser | |
| -5 1 5 | |

| acg cag ccc tgg gag cat gtg aat gcc atc cag gag gcc cgg cgt ctc | 147 |
|---|---|
| Thr Gln Pro Trp Glu His Val Asn Ala Ile Gln Glu Ala Arg Arg Leu | |
| 10 15 20 25 | |

| ctg aac ctg agt aga gac act gct gct gag atg aat gaa aca gta gaa | 195 |
|---|---|
| Leu Asn Leu Ser Arg Asp Thr Ala Ala Glu Met Asn Glu Thr Val Glu | |
| 30 35 40 | |

| gtc atc tca gaa atg ttt gac ctc cag gag ccg acc tgc cta cag acc | 243 |
|---|---|
| Val Ile Ser Glu Met Phe Asp Leu Gln Glu Pro Thr Cys Leu Gln Thr | |
| 45 50 55 | |

| cgc ctg gag ctg tac aag cag ggc ctg cgg ggc agc ctc acc aag ctc | 291 |
|---|---|
| Arg Leu Glu Leu Tyr Lys Gln Gly Leu Arg Gly Ser Leu Thr Lys Leu | |
| 60 65 70 | |

| aag ggc ccc ttg acc atg atg gcc agc cac tac aag cag cac tgc cct | 339 |
|---|---|
| Lys Gly Pro Leu Thr Met Met Ala Ser His Tyr Lys Gln His Cys Pro | |
| 75 80 85 | |

| cca acc ccg gaa act tcc tgt gca acc cag att atc acc ttt gaa agt | 387 |
|---|---|
| Pro Thr Pro Glu Thr Ser Cys Ala Thr Gln Ile Ile Thr Phe Glu Ser | |
| 90 95 100 105 | |

| ttc aaa gag aac ctg aag gac ttt ctg ctt gtc atc ccc ttt gac tgc | 435 |
|---|---|
| Phe Lys Glu Asn Leu Lys Asp Phe Leu Leu Val Ile Pro Phe Asp Cys | |
| 110 115 120 | |

| tgg gag cca gtc cag gag gcg gcc gcc ctg gag ctg cgc ccg cga tct | 483 |
|---|---|
| Trp Glu Pro Val Gln Glu Ala Ala Ala Leu Glu Leu Arg Pro Arg Ser | |
| 125 130 135 | |

| cgc tac cgt tta cag ctg cgc gcc agg ctc aac ggc ccc acc tac caa | 531 |
|---|---|
| Arg Tyr Arg Leu Gln Leu Arg Ala Arg Leu Asn Gly Pro Thr Tyr Gln | |
| 140 145 150 | |

| ggt ccc tgg agc tcg tgg tcg gac cca act agg gtg gag acc gcc acc | 579 |
|---|---|
| Gly Pro Trp Ser Ser Trp Ser Asp Pro Thr Arg Val Glu Thr Ala Thr | |
| 155 160 165 | |

| gag acc gcc tgg atc tcc ttg gtg acc gct ctg cat cta gtg ctg ggc | 627 |
|---|---|
| Glu Thr Ala Trp Ile Ser Leu Val Thr Ala Leu His Leu Val Leu Gly | |
| 170 175 180 185 | |

| ctc aac gcc gtc ctg ggc ctg ctg ctg agg tgg cag ttt cct gca | 675 |
|---|---|
| Leu Asn Ala Val Leu Gly Leu Leu Leu Arg Trp Gln Phe Pro Ala | |
| 190 195 200 | |

| cac tac agg aga ctg agg cat gcc ctg tgg ccc tca ctt cca gac ctg | 723 |
|---|---|
| His Tyr Arg Arg Leu Arg His Ala Leu Trp Pro Ser Leu Pro Asp Leu | |
| 205 210 215 | |

| cac cgg gtc cta ggc cag tac ctt agg gac act gca gcc ctg agc ccg | 771 |
|---|---|
| His Arg Val Leu Gly Gln Tyr Leu Arg Asp Thr Ala Ala Leu Ser Pro | |
| 220 225 230 | |

| ccc aag gcc aca gtc tca gat acc tgt gaa gaa gtg gaa ccc agc ctc | 819 |
|---|---|
| Pro Lys Ala Thr Val Ser Asp Thr Cys Glu Glu Val Glu Pro Ser Leu | |
| 235 240 245 | |

| ctt gaa atc ctc ccc aag tcc tca gag agg act cct ttg ccc ctg tgt | 867 |
|---|---|
| Leu Glu Ile Leu Pro Lys Ser Ser Glu Arg Thr Pro Leu Pro Leu Cys | |
| 250 255 260 265 | |

| tcc tcc cag gcc cag atg gac tac cga aga ttg cag cct tct tgc ctg | 915 |
|---|---|
| Ser Ser Gln Ala Gln Met Asp Tyr Arg Arg Leu Gln Pro Ser Cys Leu | |
| 270 275 280 | |

```
ggg acc atg ccc ctg tct gtg tgc cca ccc atg gct gag tca ggg tcc      963
Gly Thr Met Pro Leu Ser Val Cys Pro Pro Met Ala Glu Ser Gly Ser
        285                 290                 295 tgc tgt acc acc cac att gcc aac cat tcc tac cta cca cta agc tat     1011
Cys Cys Thr Thr His Ile Ala Asn His Ser Tyr Leu Pro Leu Ser Tyr
        300                 305                 310 tgg cag cag cct tga gtcgac                                           1032
Trp Gln Gln Pro
        315
```

```
<210> SEQ ID NO 9
<211> LENGTH: 334
<212> TYPE: PRT
<213> ORGANISM: Artificial Sequence
<220> FEATURE:
<221> NAME/KEY: SIGNAL
<222> LOCATION: (1)...(17)
<223> OTHER INFORMATION: Artifically synthesized human GM-CSF-human mpl
      fusion protein sequence

<400> SEQUENCE: 9
```

```
Met Trp Leu Gln Ser Leu Leu Leu Gly Thr Val Ala Cys Ser Ile
        -15                 -10                  -5

Ser Ala Pro Ala Arg Ser Pro Ser Pro Ser Thr Gln Pro Trp Glu His
  1               5                  10                  15

Val Asn Ala Ile Gln Glu Ala Arg Arg Leu Leu Asn Leu Ser Arg Asp
                 20                  25                  30

Thr Ala Ala Glu Met Asn Glu Thr Val Glu Val Ile Ser Glu Met Phe
             35                  40                  45

Asp Leu Gln Glu Pro Thr Cys Leu Gln Thr Arg Leu Glu Leu Tyr Lys
         50                  55                  60

Gln Gly Leu Arg Gly Ser Leu Thr Lys Leu Lys Gly Pro Leu Thr Met
 65                  70                  75

Met Ala Ser His Tyr Lys Gln His Cys Pro Pro Thr Pro Glu Thr Ser
 80                  85                  90                  95

Cys Ala Thr Gln Ile Ile Thr Phe Glu Ser Phe Lys Glu Asn Leu Lys
                100                 105                 110

Asp Phe Leu Leu Val Ile Pro Phe Asp Cys Trp Glu Pro Val Gln Glu
            115                 120                 125

Ala Ala Ala Leu Glu Leu Arg Pro Arg Ser Arg Tyr Arg Leu Gln Leu
        130                 135                 140

Arg Ala Arg Leu Asn Gly Pro Thr Tyr Gln Gly Pro Trp Ser Ser Trp
145                 150                 155

Ser Asp Pro Thr Arg Val Glu Thr Ala Thr Glu Thr Ala Trp Ile Ser
160                 165                 170                 175

Leu Val Thr Ala Leu His Leu Val Leu Gly Leu Asn Ala Val Leu Gly
                180                 185                 190

Leu Leu Leu Leu Arg Trp Gln Phe Pro Ala His Tyr Arg Arg Leu Arg
            195                 200                 205

His Ala Leu Trp Pro Ser Leu Pro Asp Leu His Arg Val Leu Gly Gln
        210                 215                 220

Tyr Leu Arg Asp Thr Ala Ala Leu Ser Pro Lys Ala Thr Val Ser
        225                 230                 235

Asp Thr Cys Glu Glu Val Glu Pro Ser Leu Leu Glu Ile Leu Pro Lys
240                 245                 250                 255

Ser Ser Glu Arg Thr Pro Leu Pro Leu Cys Ser Ser Gln Ala Gln Met
                260                 265                 270
```

```
Asp Tyr Arg Arg Leu Gln Pro Ser Cys Leu Gly Thr Met Pro Leu Ser
        275                 280                 285

Val Cys Pro Pro Met Ala Glu Ser Gly Ser Cys Cys Thr Thr His Ile
    290                 295                 300

Ala Asn His Ser Tyr Leu Pro Leu Ser Tyr Trp Gln Gln Pro
    305                 310                 315

<210> SEQ ID NO 10
<211> LENGTH: 1032
<212> TYPE: DNA
<213> ORGANISM: Artificial Sequence
<220> FEATURE:
<223> OTHER INFORMATION: Artificially synthesized human GM-CSF-human mpl
      fusion gene sequence
<220> FEATURE:
<221> NAME/KEY: CDS
<222> LOCATION: (22)...(1023)

<400> SEQUENCE: 10
gaattcaaag ttctctggag g atg tgg ctg cag agc ctg ctg ctc ttg ggc       51
                        Met Trp Leu Gln Ser Leu Leu Leu Leu Gly
                         1               5                  10 act gtg gcc tgc agc atc tct gca ccc gcc cgc tcg ccc agc ccc agc       99
Thr Val Ala Cys Ser Ile Ser Ala Pro Ala Arg Ser Pro Ser Pro Ser
                15                  20                  25 acg cag ccc tgg gag cat gtg aat gcc atc cag gag gcc cgg cgt ctc      147
Thr Gln Pro Trp Glu His Val Asn Ala Ile Gln Glu Ala Arg Arg Leu
            30                  35                  40 ctg aac ctg agt aga gac act gct gct gag atg aat gaa aca gta gaa      195
Leu Asn Leu Ser Arg Asp Thr Ala Ala Glu Met Asn Glu Thr Val Glu
        45                  50                  55 gtc atc tca gaa atg ttt gac ctc cag gag ccg acc tgc cta cag acc      243
Val Ile Ser Glu Met Phe Asp Leu Gln Glu Pro Thr Cys Leu Gln Thr
    60                  65                  70 cgc ctg gag ctg tac aag cag ggc ctg cgg ggc agc ctc acc aag ctc      291
Arg Leu Glu Leu Tyr Lys Gln Gly Leu Arg Gly Ser Leu Thr Lys Leu
 75                 80                  85                  90 aag ggc ccc ttg acc atg atg gcc agc cac tac aag cag cac tgc cct      339
Lys Gly Pro Leu Thr Met Met Ala Ser His Tyr Lys Gln His Cys Pro
                95                  100                 105 cca acc ccg gaa act tcc tgt gca acc cag att atc acc ttt gaa agt      387
Pro Thr Pro Glu Thr Ser Cys Ala Thr Gln Ile Ile Thr Phe Glu Ser
            110                 115                 120 ttc aaa gag aac ctg aag gac ttt ctg ctt gtc atc ccc ttt gac tgc      435
Phe Lys Glu Asn Leu Lys Asp Phe Leu Leu Val Ile Pro Phe Asp Cys
        125                 130                 135 tgg gag cca gtc cag gag gcg gcc gcc ctg gag ctg cgc ccg cga tct      483
Trp Glu Pro Val Gln Glu Ala Ala Ala Leu Glu Leu Arg Pro Arg Ser
    140                 145                 150 cgc tac cgt tta cag ctg cgc gcc agg ctc aac ggc ccc acc tac caa      531
Arg Tyr Arg Leu Gln Leu Arg Ala Arg Leu Asn Gly Pro Thr Tyr Gln
155                 160                 165                 170 ggt ccc tgg agc tcg tgg tcg gac cca act agg gtg gag acc gcc acc      579
Gly Pro Trp Ser Ser Trp Ser Asp Pro Thr Arg Val Glu Thr Ala Thr
                175                 180                 185 gag acc gcc tgg atc tcc ttg gtg acc gct ctg cat cta gtg ctg ggc      627
Glu Thr Ala Trp Ile Ser Leu Val Thr Ala Leu His Leu Val Leu Gly
            190                 195                 200 ctc aac gcc gtc ctg ggc ctg ctg ctg ctg agg tgg cag ttt cct gca      675
Leu Asn Ala Val Leu Gly Leu Leu Leu Leu Arg Trp Gln Phe Pro Ala
        205                 210                 215
```

```
cac tac agg aga ctg agg cat gcc ctg tgg ccc tca ctt cca gac ctg      723
His Tyr Arg Arg Leu Arg His Ala Leu Trp Pro Ser Leu Pro Asp Leu
        220                 225                 230 cac cgg gtc cta ggc cag tac ctt agg gac act gca gcc ctg agc ccg      771
His Arg Val Leu Gly Gln Tyr Leu Arg Asp Thr Ala Ala Leu Ser Pro
235                 240                 245                 250 ccc aag gcc aca gtc tca gat acc tgt gaa gaa gtg gaa ccc agc ctc      819
Pro Lys Ala Thr Val Ser Asp Thr Cys Glu Glu Val Glu Pro Ser Leu
                    255                 260                 265 ctt gaa atc ctc ccc aag tcc tca gag agg act cct ttg ccc ctg tgt      867
Leu Glu Ile Leu Pro Lys Ser Ser Glu Arg Thr Pro Leu Pro Leu Cys
            270                 275                 280 tcc tcc cag gcc cag atg gac tac cga aga ttg cag cct tct tgc ctg      915
Ser Ser Gln Ala Gln Met Asp Tyr Arg Arg Leu Gln Pro Ser Cys Leu
        285                 290                 295 ggg acc atg ccc ctg tct gtg tgc cca ccc atg gct gag tca ggg tcc      963
Gly Thr Met Pro Leu Ser Val Cys Pro Pro Met Ala Glu Ser Gly Ser
300                 305                 310 tgc tgt acc acc cac att gcc aac cat tcc tac cta cca cta agc tat     1011
Cys Cys Thr Thr His Ile Ala Asn His Ser Tyr Leu Pro Leu Ser Tyr
315                 320                 325                 330 tgg cag cag cct tga gtcgac                                          1032
Trp Gln Gln Pro
```

<210> SEQ ID NO 11
<211> LENGTH: 334
<212> TYPE: PRT
<213> ORGANISM: Artificial Sequence
<220> FEATURE:
<223> OTHER INFORMATION: Artificially synthesized human GM-CSF-human mpl fusion protein sequence

<400> S

```
Leu Val Thr Ala Leu His Leu Val Leu Gly Leu Asn Ala Val Leu Gly
        195                 200                 205
Leu Leu Leu Leu Arg Trp Gln Phe Pro Ala His Tyr Arg Arg Leu Arg
    210                 215                 220
His Ala Leu Trp Pro Ser Leu Pro Asp Leu His Arg Val Leu Gly Gln
225                 230                 235                 240
Tyr Leu Arg Asp Thr Ala Ala Leu Ser Pro Pro Lys Ala Thr Val Ser
                245                 250                 255
Asp Thr Cys Glu Glu Val Glu Pro Ser Leu Leu Glu Ile Leu Pro Lys
            260                 265                 270
Ser Ser Glu Arg Thr Pro Leu Pro Leu Cys Ser Ser Gln Ala Gln Met
        275                 280                 285
Asp Tyr Arg Arg Leu Gln Pro Ser Cys Leu Gly Thr Met Pro Leu Ser
    290                 295                 300
Val Cys Pro Pro Met Ala Glu Ser Gly Ser Cys Cys Thr Thr His Ile
305                 310                 315                 320
Ala Asn His Ser Tyr Leu Pro Leu Ser Tyr Trp Gln Gln Pro
                325                 330
```

<210> SEQ ID NO 12
<211> LENGTH: 17
<212> TYPE: DNA
<213> ORGANISM: Artificial Sequence
<220> FEATURE:
<223> OTHER INFORMATION: Artificially synthesized casette sequence

<400> SEQUENCE: 12
ggccccagca cagtggc                                                  17

<210> SEQ ID NO 13
<211> LENGTH: 17
<212> TYPE: DNA
<213> ORGANISM: Artificial Sequence
<220> FEATURE:
<223> OTHER INFORMATION: Artificially synthesized casette sequence

<400> SEQUENCE: 13
ggccgccact gtgctgg                                                  17

<210> SEQ ID NO 14
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 14
gggggtggac catcctcta                                                19

<210> SEQ ID NO 15
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 15
cgcgcagctg taaacggtag                                               20

CELLULAR ASSAYS FOR IDENTIFYING SIGNALING PEPTIDES

TECHNICAL FIELD

The present invention relates to the field of genetic engineering and includes methods for detecting and isolating nucleic acid sequences encoding peptides that contain signal sequences.

BACKGROUND ART

So far, genes encoding a hormone or growth factor have been isolated and utilized to produce many recombinant proteins that are commercialized as medicines. Most of them are secretory proteins. Therefore, isolation of a gene encoding a novel secretory protein is an extremely important step in developing a novel medicine. Accordingly, methods for isolating a gene encoding a secretory protein have been developed. For example, Honjo et al. developed a method (unexamined published Japanese patent application No. Hei 6-315380) by utilizing the feature that secretory proteins have a signal sequence that allows intracellularly expressed proteins to translocate to the cell surface. In this method, the signal sequence of the α chain of human IL-2 receptor, a secretory protein, is replaced with a short cDNA fragment corresponding to the 5'-end sequence of mRNA from a target cell or tissue to construct a library, which is then introduced into cells. Among the clones, IL-2 receptor is expressed on the cell surface of clones with a signal sequence, but not those without a signal sequence. The presence of the signal sequence can thus be detected by the anti-IL-2 receptor antibody.

Genetics Institute, Inc., (Cambridge, Mass.) developed a more sophisticated system utilizing a yeast metabolic enzyme (U.S. Pat. No. 5,536,637). Invertase, a yeast metabolic enzyme, is a secretory enzyme that cleaves sucrose in the culture medium to glucose and fructose to transfer energy. A mutant strain that does not secrete this enzyme can not grow in a medium containing sucrose as the sole carbon source without glucose. In this method, which utilizes the phenomenon, invertase gene is ligated with cDNA to construct a library, which is then introduced into a mutant yeast strain lacking the invertase gene. Clones containing the signal peptide are isolated by selecting clones capable of growing in a medium containing only sucrose as a carbon source.

However, the method of Honjo et al. is disadvantageous in that laborious steps are required in selecting positive clones due to the use of an antibody. Furthermore, the detection sensitivity is very low. The method of Genetics Institute, Inc., also has a problem in that a clone with poor secretion efficiency in yeast cannot be isolated. In addition, these methods detect only short DNA because of the potential loss of antigenicity or enzymatic activity when the reporter protein is fused with a large protein. Moreover, the methods fail to detect the type II membrane proteins having their N-terminus within the cell and C-terminus outside the cell.

DISCLOSURE OF THE INVENTION

The present invention provides a method for determining whether or not a tested cDNA encodes a peptide that has secretory activity. The methods also provide for isolating a cDNA encoding a peptide with secretory activity, which can be done using a cDNA encoding a peptide longer than the signal sequence.

Proteins, such as cytokine receptors, translocate to the cell surface, dimerize upon binding their ligands, and induce cell proliferation. The proteins that are translocated to the cell surface are guided by a signal sequence. The present inventors discovered that it was possible to determine whether a desired peptide has secretory activity by removing the signal sequence (and, optionally, additional sequence that encodes an extracellular region of the peptide) from the proteins that translocate to the cell surface and replacing that signal sequence with a desired peptide, thereby creating a sequence encoding a fusion protein, expressing the fusion protein in cells, and examining the proliferation of the cells. If the desired peptide has secretory ability, the fusion protein translocates to the cell surface, dimerizes, and induces cell proliferation. In contrast, if the desired peptide does not have secretory activity, the fusion protein cannot translocate to the cell surface and induce cell proliferation. Thus, one can determine whether a desired peptide has the ability to mediate translocation by simply examining cell proliferation as an index. Moreover, the inventors discovered a way to perform positive screening for a peptide that has secretory ability by selecting cells that proliferate. Thus, the present inventors used mpl (thrombopoietin receptor) as a protein that triggers cell proliferation through translocation to the cell surface and dimerization, and developed a method for detecting and isolating peptides possessing secretory ability.

Specifically, we prepared a DNA encoding human mpl without the secretory ability by removing the secretion signal and most of the extracellular domain from a constitutively active form of mpl, which was found by the present inventors (the mpl is altered to be able to confer autonomous proliferation ability to an IL-3 dependent cell line by the transducing signal in the absence of ligand; Blood 88:1399–1406 (1996)). The DNA was then ligated with cDNA to be tested, a DNA encoding a known secretory protein, or a DNA encoding the secretory peptide from which the secretory signal region was removed. The resulting chimeric genes were expressed in cells, and the proliferation ability of the cells was examined. The results show that the DNA encoding a known secretory protein used as a test cDNA induced cell proliferation whereas no cell proliferation was detected for the DNA encoding the secretory protein from which the secretory signal region was removed. In this way, the inventors found that the system thus developed can be used to easily detect and isolate a DNA encoding a peptide with secretory activity and containing a long peptide coding region using cell proliferation as an index. Indeed, they performed a screening and succeeded in detecting and isolating DNAs encoding secretory proteins including type I membrane proteins and type II membrane proteins.

Thus, the present invention relates to:

(1) a peptide capable of inducing cell proliferation through dimerization on the cell surface and lacking the secretory ability;
(2) the peptide as described in (1), wherein the peptide is derived from a cytokine receptor;
(3) the peptide as described in (1), wherein the peptide is derived from mpl;
(4) the peptide as described in (2) or (3), wherein the peptide is ligand-independent;
(5) the peptide as described in (1), wherein the peptide comprises the amino acid sequence of SEQ ID NO: 4;
(6) a DNA encoding the peptide as described in any of (1) to (5);
(7) a vector containing the DNA as described in (6) and a cloning site for cDNA at the 5'-upstream region of the DNA;
(8) the vector as described in (7), wherein the vector is derived from a retrovirus;
(9) the vector described in (7) or (8), wherein a cDNA is inserted into the 5'-upstream of the DNA of (6);
(10) a cell carrying the vector as described in (9);

(11) a cell as described in (10), wherein the cell is a mammalian cell;

(12) a method for examining whether a peptide encoded by a cDNA to be tested contains the secretory ability, the method comprising
  (a) ligating the test cDNA with the vector of (7),
  (b) introducing the vector prepared in (a) into a cell, and
  (c) culturing the transformant prepared in (b), and detecting the cell proliferation ability;

(13) a method for isolating a cDNA encoding a peptide with the secretory ability, the method comprising
  (a) ligating a cDNA library with the vector of (7),
  (b) introducing the vector prepared in (a) into a cell,
  (c) culturing the transformant prepared in (b), and detecting the cell proliferation ability, and
  (d) selecting a positive cell that is judged to have cell proliferation ability in (c), and isolating the DNA from said cell;

(14) a method as described in (12) or (13), wherein the vector is derived from a retrovirus and the cell to be introduced with the vector is a mammalian cell;

(15) a cDNA encoding a peptide with the secretory ability, which is isolated by the method of (13); and (16) a peptide encoded by the DNA as described in (15).

The present invention relates to a method for detecting a DNA encoding a peptide having secretory ability. The detection method features the use of a DNA encoding a peptide that induces cell proliferation when dimerized on the cell surface but that lacks its secretory signal. This peptide can be used to detect a peptide with secretory ability. Here, "the peptide that induces, or that is capable of inducing, cell proliferation through dimerization on the cell surface" includes mpl (Proc. Natl. Acad. Sci. USA, 89:5640–5644 (1992)), the alpha chain or beta chain of GM-CSF receptor (Blood 83:2802 (1994)), erythropoietin receptor (Nature 348:647 (1990)), c-kit receptor (Blood 85:790 (1995)), and neu (Nature 339:230 (1989)), but are not limited thereto. In the method of the present invention, a cDNA is constructed to encode the above peptides whose secretory ability is eliminated. The secretory ability is usually removed by deleting a region containing the signal sequence. For example, the signal sequence of the human mpl is the region corresponding to positions 1 to 25 in the amino acid sequence of the protein (Proc. Natl. Acad. Sci. USA, 89:5640–5644 (1992)), and that of the beta chain of the human GM-CSF receptor is the region corresponding to positions 1 to 48 (Proc. Natl. Acad. Sci. USA, 87:9655–9659 (1990)). Preferably, the extracellular domain is also deleted from the peptide.

The peptide encoded by a constructed cDNA is preferably ligand-independent (if the peptide is ligand-dependent, it may lose the ligand-binding ability and become inactive after creating a fusion protein). A method for creating a ligand-independent peptide is to introduce a mutation into the peptide. For example, in the case of mpl, the substitution of Ser at position 498 with Asn can abolish the dependency of mpl on its ligand, thrombopoietin (Blood 88:1399–1406 (1996)). The mpl used in the present method preferably comprises the amino acid sequence as described in SEQ ID NO: 4.

The DNA prepared as described above is inserted into an appropriate expression vector. The expression vector is not limited, and can be a retroviral vector, which can be introduced into a variety of cells with high efficiency through virus infection. Upon expression, the DNA inserted into the vector is stably expressed in the cells. Examples of retroviral vectors include those engineered for cDNA library construction, such as pBabeX (Proc. Natl. Acad. Sci. USA 92:9146–9150 (1995)) or pMX (Exp. Hematol. 24:324–329 (1996)). One can also use viral vectors such as adenovirus, EB virus, and papilloma virus, or plasmid vectors such as pEF-BOS (Nucleic Acid Res. 18 (17)) and pcD SRα296 (Mol. Cell. Biol. January 466–472 (1988)). The expression vectors can have a cloning site for a cDNA to be tested for its secretory ability at the 5'-upstream region of the above DNA insert (i.e., upstream of the sequence encoding the protein that, when under the control of its own signal sequence, is translocated to the cell membrane); upon expression, the sequence encodes a fusion protein of the test signal sequence and the translocatable protein that lacks its own signal sequence. The method for creating a cloning site for a cDNA is known to one of ordinary skill in the art.

As noted above, the prepared vector can include a cDNA to be tested. The test cDNA is ligated into the 5'-upstream region of the DNA that encodes a peptide that induces cell proliferation upon dimerization on the cell surface, which is inserted into the vector. The test cDNA can be any cDNA encoding a peptide whose secretory ability is to be tested. The test cDNA can be ligated with a vector according to standard methods. For example, the ligation method using T4 DNA ligase via an adapter linker (Maniatis T., Molecular Cloning).

The prepared vector is then introduced into a cell. Cells into which the vector is introduced are not limited and include cytokine-dependent proliferating cell such as Ba/F3, OTT-1, FDCP-1, and TF-1 cells. Vectors can be introduced into cells by using standard methods including lipofection, calcium phosphate method, DEAE-dextran method, and electroporation. In retrovirus infection-mediated introduction, the vector is introduced into the packaging cells and integrated into the virus particles. The vector can be introduced by using standard methods such as the calcium phosphate method and lipofection. For example, cells such as BOSC23, Bing (Proc. Natl. Acad. Sci. USA 90:8392–8396 (1993)), NX-E, and NX-A cells (Nolan G. P. Immunity 8:461–471 (1998)) can be used as the packaging cell.

Next, the thus-prepared transformants are cultured and examined for their proliferation ability. When a protein encoded by cDNA inserted into the vector is expressed as a fusion protein with a ligand-independent active cytokine receptor, the transformant is cultured in the medium lacking the cytokine (ligand) on which the cell depends. If a significant cell proliferation is detected, the test cDNA is judged to be a "positive clone" encoding a peptide that contains the secretory ability. Alternatively, if no significant cell proliferation is detected, the cDNA is judged to be a "negative clone" that encodes a peptide lacking the secretory ability. When a protein encoded by the inserted cDNA is expressed as a fusion protein with a ligand-dependent cytokine receptor, the transformant is cultured in the presence of the ligand. If a significant cell proliferation is detected, after comparison with a negative control in the absence of the ligand, if necessary, the test cDNA is judged to be a "positive clone." Other conditions for culturing transformants can be appropriately selected by one skilled in the art depending on the types of cells into which the vector is inserted and the nature of the fusion protein to be expressed.

The present invention also relates to a method for isolating a cDNA encoding a peptide that contains the secretory ability. In the method, a cDNA library is ligated into the vector instead of the above test cDNA that is used for detecting cDNA encoding a peptide containing the secretory ability. In one specific embodiment of the invention, cDNAs prepared by using a random primer are ligated with the BstXI adapter and inserted between the two BstXI sites; one is of the vector and the other is inserted into the extracellular cleavage site of the active mpl. The source of the cDNA library is not limited to any specific one, but can be a cell or tissue from which a desired peptide containing the secretory ability is to be isolated. Many standard methods can be used to construct a cDNA library. In the present method, cells judged to be capable of proliferation are selected from the cDNA library-introduced cells. The cDNAs contained in the selected cells are supposed to encode a peptide having the secretory ability. cDNA can be isolated from the cells whose proliferation has been detected by, for example, extracting the genomic DNA or RNA, amplifying the cDNA of interest by PCR using primers designed to encompass the cloning sites (in case of RNA, after converting it into DNA-using reverse transcriptase), and recovering the products.

Whether the recovered cDNA is full length or a fragment, or whether it is a cDNA encoding a novel secretory peptide, can be analyzed by comparing the cDNA sequence with those of the known proteins in the database. If the cDNA is not full length, it is used to screen a secondary cDNA library to isolate a full-length cDNA. The secondary cDNA library can be constructed by a method known to one skilled in the art, such as those described in the literature (Molecular Cloning, A Laboratory Manual, 2nd edition. Sambrook J. et al., (1989) Cold Spring Harbor Laboratory Press, New York).

A cDNA encoding a peptide with the secretory ability isolated by the method of the present invention can be utilized to produce a recombinant protein that is useful as a medicine or in gene therapy of related diseases. A recombinant protein from the isolated cDNA can be produced by known methods in the art. For example, the cDNA is inserted into an appropriate vector such as pED (Kaufman et al. Nucleic Acids Res. 19:4484–4490 (1991)), pEF-BOS (Mizushima et al. Nucleic Acids Res. 18:5322 (1990)), pXM, pJl3, and pJL4 (Gough et al. EMBO J. 4:645–653 (1985)), the vector is introduced into a host cell, the resulting transformant is cultured to allow it to express a recombinant protein, and the recombinant protein is purified.

BEST MODE FOR CARRYING OUT THE INVENTION

The present invention is illustrated in detail below with reference to examples, but is not to be construed as being limited thereto.

EXAMPLE 1

Vector Construction

In mouse myeloproliferative leukemia virus, env is ligated to the mouse mpl comprising the extracellular domain consisting of 56 amino acids from the transmembrane domain toward the N-terminus, the transmembrane domain, and the intracellular domain. PCR was performed to obtain a cDNA encoding the corresponding region of the human mpl, which is from Leu (449) to the stop codon (636), having the NotI site immediately before the Leu (449) (a single nucleotide insertion) and the SalI site immediately after the stop codon so as to be in the frame of the GM-CSF cDNA shown below. The "pBabeX MPL$^M$" (Blood 88:1399–1406. (1996)), in which active human mpl cDNA is cloned, was used as a template. Primers used are listed in Table 1.

TABLE 1

Not v-mpl (SEQ ID NO: 1)
(T<u>GCGGCCGC</u>CCTGGAGCTGCGCCCGCGATCCTGCTACCGTTTA)
   NotI        the sequence of mpl MPL Sal (SEQ ID NO: 2)
(GTAT<u>GTCGAC</u>TCAAGGCTGCTGCCAATAG)
    SalI PCR was performed in a reaction mixture containing 10 μg/ml template DNA, 1 μM each primer, 50 U/ml KOD DNA polymerase (TOYOBO), 1 mM MgCl$_2$, 0.2 mM dNTPs, 120 mM Tris-HCl (pH 8), 10 mM KCl, 6 mM (NH$_4$)$_2$SO$_4$, 0.1% Triton X-100, and 10 μg/ml BSA by using the GeneAmpPCR System (Perkin Elmer) under the following conditions: denaturation at 98° C. for 60 sec, followed by 25 cycles of 98° C. for 15 sec, 60° C. for 10 sec, and 74° C. for 30 sec. The PCR products were analyzed by electrophoresis on an agarose gel, and a gel piece containing a 0.6 kb fragment of interest was excised to extract DNA. The DNA was then phosphorylated at its 5'-termini with T4 polynucleotide kinase (TOYOBO), and ligated by using T4 DNA ligase (TOYOBO) with the pBluescript SK(-) vector (Stratagene) that was pretreated with SmaI (TaKaRa Shuzo) and Bacterial Alkaline Phosphatase (BAP; TaKaRa Shuzo). The nucleotide sequence of the active mpl cDNA inserted in the resulting plasmid was verified with the ABI PRISM 310 Genetic Analyzer (Perkin Elmer). The plasmid was digested with NotI (TaKaRa Shuzo) and SalI (TaKaRa Shuzo), and separated by electrophoresis on an agarose gel to isolate a 0.6 kb fragment. The fragment was ligated with the pMX (Proc. Natl. Acad. Sci. USA 92:9146–9150. (1995)), which was also digested with NotI and SalI, treated with BAP, and purified by agarose gel electrophoresis, using T4 DNA ligase to obtain pMX v-mpl$^M$. The plasmid pMX v-mpl$^M$ contains a cDNA encoding an active mpl lacking the secretory ability. The nucleotide sequence of the cDNA insert and the amino acid sequence of the peptide encoded by the cDNA are shown in SEQ ID NO: 3 and NO: 4, respectively.

Next, to obtain a human GM-CSF cDNA in which the stop codon is replaced with a NotI site, PCR was performed by using the pcDSRα 298 hGM-CSF (Proc. Natl. Acad. Sci. USA 82:4360–4364 (1985)) containing the human GM-CSF cDNA as a template. Primers used are shown in Table 2.

TABLE 2

| | | |
|---|---|---|
| EcoGMss | (SEQ ID NO: 5) | (C<u>GAATTC</u>AAAGTTCTCTGGAGGATG)<br>  EcoRI |
| EcoGM | (SEQ ID NO: 6) | (C<u>GAATTC</u>GCCGCCACCATGGCACCCGCCCGCTCGCCC)<br>  EcoRI |
| GM Not | (SEQ ID NO: 7) | (A<u>GCGGCCGC</u>CTCCTGGACTGGCTCCCA)<br>  NotI |

EcoGM was designed to have the translation initiation codon ATG in place of the Ser (17), and, as in EcoGMss and EcoGM, the EcoRI site and the Kozak consensus sequence (J. Cell Biol. 108:29. (1989)) immediately before the ATG codon. Primer pairs of EcoGMss and GM Not were used in PCR to amplify GM-CSF containing the signal sequence, and EcoGM and GM Not were used to amplify GM-CSF lacking the signal sequence. PCR was performed as described above except for using 55° C. for the annealing temperature, and the products were cloned into the pBluescript SK(-). The nucleotide sequence of the DNA inserts was verified by using the ABI PRISM 310 Genetic Analyzer (Perkin Elmer). The plasmids were then digested with EcoRI (TaKaRa) and NotI and inserted into the EcoRI-NotI site of the pMX v-mpl$^M$ as described above, and "pMX GM(+)v-mpl$^M$" and "pMX GM(-)v-mpl$^M$" were obtained. The "pMX GM(+)v-mpl$^M$" and "pMX GM(-)v-mpl$^M$" encode a fusion protein between the C-terminal part of the active mpl starting from Leu (449) and the entire GM-CSF with or without the signal sequence, respectively. The nucleotide sequences of their cDNA inserts are shown as SEQ ID NO: 8 and NO: 10, and the amino acid sequences of the proteins encoded by the cDNAs are shown as SEQ ID NO: 9 and NO: 11.

EXAMPLE 2

Viral Infection

Each of the above plasmids was introduced into packaging cell-line BOSC23 (Proc. Natl. Acad. Sci. USA 90:8392–8396. (1993)) using LipofectAMINE (Life Technologies). BOSC23 cells were plated into 6-cm dishes (CORNING) with Dulbecco's modified Eagle medium (DMEM; Nissui Pharmaceutical) containing 10% fetal calf serum (FCS; JRH Biosciences). After 6-hr incubation, the cells were washed with OPTI-MEM I reduced serum medium (Life Technologies). Separately, LipofectAMINE (18 µl) diluted in 200 µl OPTI-MEM I was mixed with 3 µg samples of each plasmid diluted in 200 µl OPTI-MEM I. The resulting mixtures were allowed to stand at room temperature for 15 minutes, mixed with 1.6 ml OPTI-MEM I, then added to the cells. After 5 hr, 2 ml of DMEM containing 20% FCS was added to the cells, which were incubated for an additional 19 hr. The medium was then replaced with 3 ml of DMEM containing 10% FCS, and the culture supernatant was recovered after 24 hr. Mouse interleukin-3 (IL-3) and 10 µg/ml polybrene (hexadimethrine bromide, Sigma) were added to the culture supernatant containing the recombinant virus, and Ba/F3 cells were suspended therein for infection. After 24 hr of infection, the cells were washed twice in RPMI1640 (Nissui Pharmaceutical) containing 10% FCS lacking mouse IL-3, and the culture was continued in the same medium.

Figure 1:
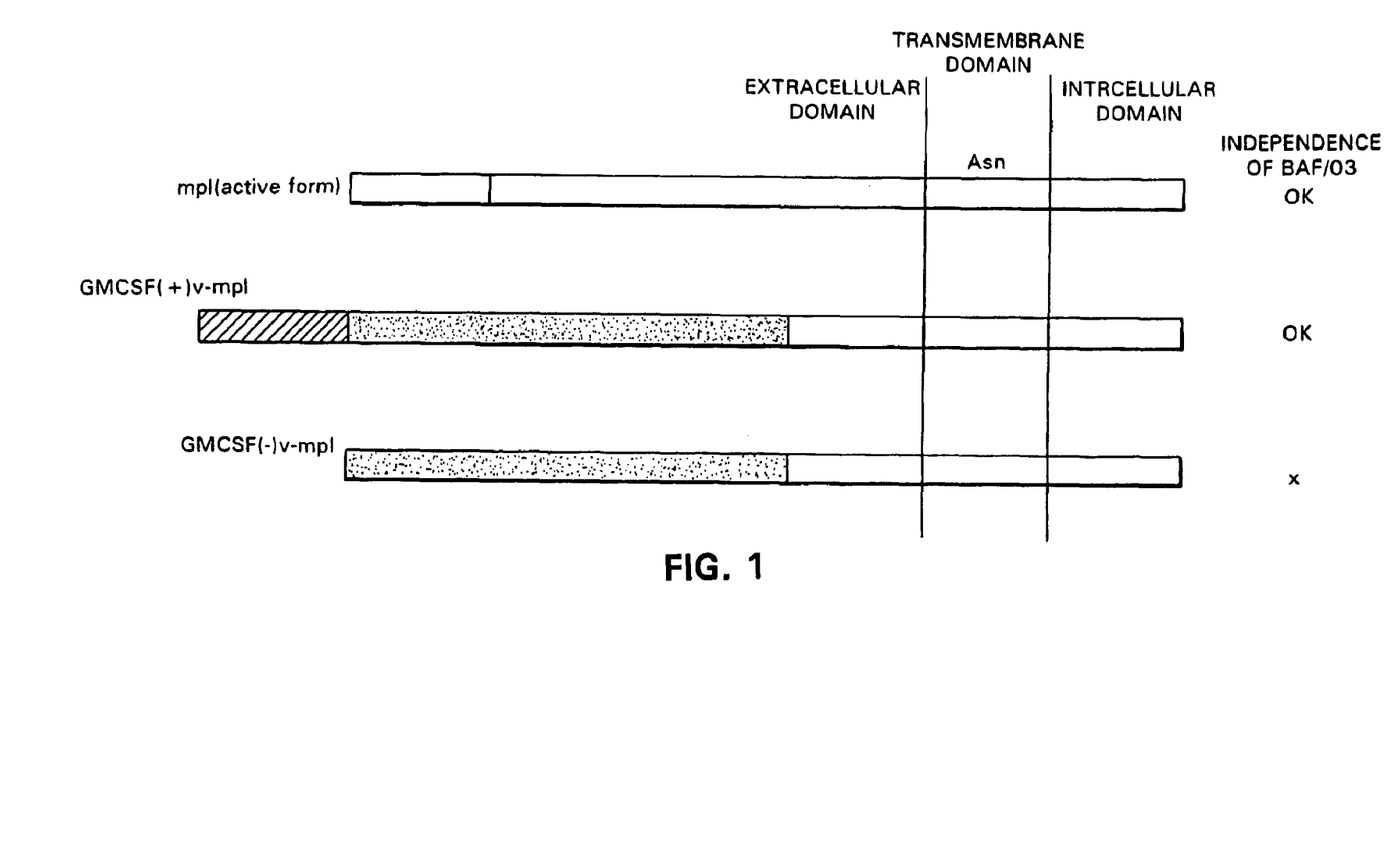
FIG. 1 is a schematic representation of the peptides used for detecting secretory ability and the detection of cytokine-independent proliferation ability of BAF/03 cells through the expression of the peptides. This figure shows active mpl (Ser498Asn) induced factor-independent proliferation. The full-length human GM-CSF receptor with secretory ability, which is fused to the C-terminal 187 amino acid portion of active mpl, also induced factor-independent proliferation. In contrast, GM-CSF receptor lacking the signal sequence did not induce cell proliferation.

The cells containing the fusion protein between the entire GM-CSF containing the signal sequence and the active mpl (derived from the pMX GM(+)v-mpl$^M$) grew in the absence of IL-3 as well as those containing the active mpl with the secretory ability. In contrast, the cells containing the fusion protein between the GM-CSF lacking the signal sequence and the active mpl (pMX GM(-)v-mpl$^M$) did not grow as well as control Ba/F3 cells into which no fusion protein expression vector was introduced (FIG. 1).

EXAMPLE 3

Screening

The following oligonucleotides (Table 3) were synthesized, and their 5'-termini were phosphorylated using T4 polynucleotide kinase. The oligonucleotides were mixed and denatured at 95° C., and then annealed by gradually cooling them to 40° C. to prepare the cassette DNA.

TABLE 3

| | |
|---|---|
| 5'-GGCCCCAGCACAGTGGC-3' | (SEQ ID NO: 12) |
| 5'-GGCCGCCACTGTGCTGG-3' | (SEQ ID NO: 13) |

The pMX GM(-)v-mpl$^M$, which was digested with NotI (TaKaRa) and treated with BAP, was mixed with the cassette and ligated using T4 DNA ligase. The direction of the cassette in the resulting plasmid was verified by DNA sequencing to be in the order of BstXI and NotI (pMX GM(-)v-mpl$^{M2}$). Total RNA was prepared from the rat neuroblastic cell line MNS70 using the TRIZOL reagent (GIBCO BRL) and passed through the oligo dT column (Pharmacia) to prepare polyA(+) RNA. Double-stranded cDNA was synthesized with the random hexamer contained in the SuperScript Choice System (GIBCO BRL). The cDNA was blunt-ended, ligated with the BstXI adapter (Invitrogen), and fractionated by using the SizeSep 400 Spun Column (Pharmacia). The cDNA was then mixed and ligated with the pMX GM(-)v-mpl$^{M2}$ which was digested with BstXI (TaKaRa) and treated with BAP, using T4 DNA ligase. The DNA was introduced into DH10B E. coli (GIBCO BRL) by electroporation using Gene Pulser (BioRad) to construct a cDNA library.

Plasmids were extracted from the recombinant E. coli containing a cDNA library and purified by using the JETstar column (GENOMED). The library plasmids were introduced into BOSC23 packaging cells by using LipofectAMINE as described above. Mouse IL-3 (10 ng/ml) and 10 µg/ml polybrene (Hexadimethrine Bromide, Sigma) were added to the culture supernatant containing the recombinant virus, and Ba/F3 cells were suspended therein for infection. After 24-hr infection, the cells were washed twice with phosphate buffer and cultured further in RPMI1640 containing 10% FCS. The genomic DNA was prepared from the clones that grew in the absence of IL-3, and PCR was performed using primers designed to encompass the cDNA insertion site to recover the cDNA fragments.

TABLE 4

| | |
|---|---|
| 5'-GGGGGTGGACCATCCTCTA-3' | (SEQ ID NO: 14) |
| 5'-CGCGCAGCTGTAAACGGTAG-3' | (SEQ ID NO: 15) |

PCR was performed in 50 µl of the reaction mixture containing 500 ng genomic DNA, 500 pM each primer, 2.5 U TaKaRa LA Taq (TaKaRa), 2.5 mM MgCl$_2$, 0.3 mM dNTPs, and the accompanying buffer using the GeneAmp-PCR System2400 in the following process: denaturation at 98° for 60 sec, followed by 30 cycles of 98° for 20 sec and 68° for 120 sec. PCR products were separated by electrophoresis on an agarose gel, the gel pieces containing the amplified fragments were excised, and DNA was purified. The nucleotide sequence of the DNA fragments purified from the resulting 190 clones was determined, and 150 clones were found to be cDNAs encoding a known secretory protein or a membrane protein, or parts thereof. The other 40 clones were found to encode unknown secretory proteins. Some of the thus-obtained known secretory proteins are shown in Table 5, where "length" indicates the length of the ORF of the obtained cDNA fragment by the number of amino acid residues. The average length of the clones encoding a known secretory protein was 273 amino acid residues. "Accession number" indicates the accession number in the GenBank protein database. It should be noted that the background in the present method such as detecting a cDNA encoding a protein other than a secretory protein or cDNA that was inserted in the opposite direction was 1% or less.

TABLE 5

| Length | Accession No. | Name |
|---|---|---|
| 221 | 1805299 | Amyloid precursor |
| 288 | 416630 | Amyloid-like protein 1 |
| 350 | 466563 | Amyloid precursor-like protein 2 |
| 561 | 112929 | Amyloid A4 protein homologue precursor |
| 161 | 2494287 | o-acetyl GD3 ganglioside synthase |
| 176 | 2507439 | Syndecan 3 (heparan sulfate proteoglycan core protein) |
| 218 | 118115 | Cyr61 protein (growth factor binding protein) |
| 382 | 3219172 | collagen alpha 1(V) |
| 286 | 461671 | collagen alpha 1 type 1 |
| 159 | 1082724 | Prostacyclin-stimulating factor |
| 259 | 1777354 | SHPS-1, BIT |
| 254 | 205167 | 120 kDa sialoglycoprotein (a hepatic lysosomal membrane protein) |
| 482 | 1708023 | K-glypican |
| 224 | 1139548 | Seizure-related gene product 6 type2 precursor |
| 105 | 135818 | G-protein coupled thrombin receptor |
| 482 | 129731 | Protein Disulfide Isomerase |
| 322 | 1172451 | perlecan (basement membrane heparin sulfate proteoglycan) |
| 165 | 1709256 | neurocan (proteoglycan core protein - precursor) |
| 264 | 2367641 | neuropilin-2 (semaphorin III receptor) |
| 211 | 126638 | Lysyl oxidase |
| 308 | 2627143 | Neural cadherin |
| 459 | 3123675 | Notch |
| 140 | 1718156 | Vascular endothelial growth factor |
| 534 | 627989 | Endothelin-converting enzyme |
| 89 | 114393 | Sodium/potassium-transporting ATPase beta-1 chain |

INDUSTRIAL APPLICABILITY

The present invention provides a method for detecting and isolating a cDNA encoding a secretory peptide using a peptide capable of triggering cell proliferation through its dimerization on the cell surface but lacking the secretory ability. Since the method utilizes cell proliferation as an index for detection, it is extremely easy and sensitive. Moreover, compared to the conventional methods that enable detecting a short DNA fragment, this method enables detecting and isolating a cDNA containing a longer peptide coding region, and thus provides more information from the first isolated clones. In addition, the method enables detecting and isolating secretory proteins including type I and type II membrane proteins.

What is claimed is:

1. A method for determining whether a test polypeptide encoded by a test nucleic acid sequence has a secretory signal region, the method comprising
   (a) providing a vector comprising
      (i) a first nucleic acid sequence encoding a portion of a translocatable protein that induces cell proliferation upon dimerization on a cell surface, wherein the portion of the translocatable protein lacks a secretory signal region present in the full-length translocatable protein; and
      (ii) a second nucleic acid sequence encoding a test polypeptide, wherein the second nucleic acid sequence is ligated to the first nucleic acid sequence such that expression of the vector produces a fusion protein comprising the portion of the translocatable protein and the test polypeptide;
   (b) introducing the vector into a host cell to produce a genetically engineered cell;
   (c) culturing the genetically engineered cell under conditions that permit expression of the fusion protein; and
   (d) detecting proliferation of the genetically engineered cell, wherein proliferation greater than that of a control cell indicates that the test polypeptide has a secretory signal region.

2. The method of claim 1 wherein the vector is a retroviral vector and the cell is a mammalian cell.

3. The method of claim 1, wherein the vector is a retroviral vector and the cell of (b) is a cytokine-dependent proliferating cell.

4. An expression vector comprising a nucleic acid sequence encoding a polypeptide that:
   (a) comprises the sequence of a protein selected from the group consisting of an mpl, a beta chain of a granulocyte-macrophage colony-stimulating factor (GM-CSF) receptor, an erythropoietin (EPO) receptor, a c-kit receptor, neu, and an fms-like tyrosine kinase-3 (FLT-3);
   (b) lacks the secretory signal region of the protein; and
   (c) comprises a second sequence encoding a polypeptide that is not the secretory signal region of the protein.

5. The vector of claim 4, wherein the vector is a retroviral vector.

6. A cell comprising the vector of claim 4.

7. The cell of claim 6, wherein the cell is a mammalian cell.

8. The cell of claim 6, wherein the cell is a cytokine-dependent proliferating cell.

9. A method for determining whether a test polypeptide has a secretory signal region, the method comprising
   (a) providing a cell comprising a vector, wherein the vector comprises a nucleic acid sequence that encodes a fusion protein comprising a test polypeptide and a translocatable polypeptide, wherein the translocatable polypeptide
      (i) lacks a secretory signal region, and
      (ii) induces cellular proliferation when dimerized on the surface of the cell; and
   (b) detecting proliferation of the cell, wherein proliferation greater than that of a control cell indicates that the test polypeptide has a secretory signal region.

10. The method of claim 9, wherein the vector is a retroviral vector and the cell is a mammalian cell.

11. The method of claim 9, wherein the translocatable polypeptide comprises a cytokine receptor.

12. The method of claim 9, wherein the translocatable polypeptide is an mpl, a beta chain of a GM-CSF receptor, an EPO receptor, a c-kit receptor, neu, or FLT-3.

13. The method of claim 9, wherein the translocatable polypeptide is ligand-independent.

14. The method of claim 9, wherein the translocatable polypeptide dimerizes upon binding to its ligand.

15. The method of claim 9, wherein the vector is a retroviral vector and the cell is a cytokine-dependent proliferating cell.

16. A method of isolating a nucleic acid encoding a polypeptide having a secretory signal region, the method comprising
   (a) providing a cell comprising a vector, wherein the vector comprises a nucleic acid sequence that encodes a fusion protein comprising
      (i) a test polypeptide, and
      (ii) a translocatable polypeptide that induces cellular proliferation when dimerized on the surface of the cell;
   (b) detecting proliferation of the cell, wherein proliferation greater than that of a control cell indicates that the test polypeptide has a secretory signal region; and
   (c) if proliferation is greater than that of the control cell, isolating the nucleic acid from the cell.

17. The method of claim 16, wherein the vector is a retroviral vector and the cell is a mammalian cell.

18. The method of claim 16, wherein the translocatable polypeptide comprises part or all of a cytokine receptor.

19. The method of claim 16, wherein the translocatable polypeptide is an mpl, a beta chain of a GM-CSF receptor, an EPO receptor, a c-kit receptor, neu, or FLT-3.

20. The method of claim 16, wherein the translocatable polypeptide is ligand-independent.

21. The method of claim 16, wherein the translocatable polypeptide dimerizes upon binding to its ligand.

22. The method of claim 16, wherein the vector is a retroviral vector and the cell is a cytokine-dependent proliferating cell.

23. A method for isolating a nucleic acid encoding a polypeptide having secretory activity, the method comprising
   (a) providing a vector comprising
      (i) a first nucleic acid sequence encoding a portion of a translocatable protein that induces cell proliferation upon dimerization on a cell surface, wherein the portion of the translocatable protein lacks a secretory signal region present in the full-length translocatable protein; and
      (ii) a second nucleic acid sequence encoding a test polypeptide, wherein the second nucleic acid sequence is ligated to the first nucleic acid sequence such that expression of the vector produces a fusion protein comprising the portion of the translocatable protein and the test polypeptide;
   (b) introducing the vector into a cell to produce a genetically engineered cell;
   (c) culturing the genetically engineered cell under conditions that permit expression of the fusion protein;
   (d) detecting proliferation of the genetically engineered cell; and
   (e) isolating the nucleic acid from the genetically engineered cell if the genetically engineered cell proliferates more than a control cell.

24. An isolated nucleic acid encoding a polypeptide that:
   (a) comprises the sequence of a protein selected from the group consisting of an mpl, a beta chain of a granulocyte-macrophage colony-stimulating factor (GM-CSF) receptor, an erythropoietin (EPO) receptor, a c-kit receptor, neu, and an fms-like tyrosine kinase-3 (FLT-3); and (b) lacks the secretory signal region of the protein.

25. An isolated nucleic acid encoding a fusion protein comprising (a) a first polypeptide having the sequence of a protein selected from the group consisting of an mpl, a beta chain of a GM-CSF receptor, an EPO receptor, a c-kit receptor, neu, and an FLT-3 and lacking the secretory signal sequence of the polypeptide; and (b) a second polypeptide that is not the secretory signal region of the protein.

26. An isolated nucleic acid comprising a sequence encoding (a) SEQ ID NO:4 or (b) a fusion protein comprising SEQ ID NO:4, wherein the fusion protein does not contain the secretory signal region of mpl.

27. An expression vector comprising the nucleic acid of claim 26.

28. The vector of claim 27 that is a retroviral vector.

29. A cell comprising the vector of claim 27.

30. The cell of claim 29 that is a mammalian cell.

* * * * *

UNITED STATES PATENT AND TRADEMARK OFFICE
CERTIFICATE OF CORRECTION

PATENT NO. : 6,866,998 B1
DATED : March 15, 2005
INVENTOR(S) : Tetsuo Kojima and Toshio Kitamura

It is certified that error appears in the above-identified patent and that said Letters Patent is hereby corrected as shown below:

Title page,
Item [56], References Cited, OTHER PUBLICATIONS,
"Livnah et al. Functional mimicry of a protein hormone by a peptide agonist: The EPO receptor complex at 2.8 A (1996), Scienc vol. 273, pp 464-471.*" to
-- Livnah et al. Functional mimicry of a protein hormone by a peptide agonist: The EPO receptor complex at 2.8 A (1996), Science vol. 273, pp 464-471.* --;
"Onishi et al., "Identification of an Oncogenic Form of the Thrombopoietin Receptor MPL Uing Retrovirus-Mediated Gene Transfer", Blood 88:1399-1406 (1996)." to
-- Onishi et al., "Identification of an Oncogenic Form of the Thrombopoietin Receptor MPL Using Retrovirus-Mediated Gene Transfer", Blood 88:1399-1406 (1996). --;
"Vigon et al., "Molecular cloning and characterization of MPL, the human homolog of the v-mpl oncogene: Identification of a member of the hematopoietic growth factor receptor superfamily", Pro. Natl. Acad. Sci. USA 89:5640-5644 (1992)." to
-- Vigon et al., "Molecular cloning and characterization of MPL, the human homolog of the v-mpl oncogene: Identification of a member of the hematopoietic growth factor receptor superfamily", Proc. Natl. Acad. Sci. USA 89:5640-5644 (1992). --; and Drawings,
FIG. 1, amend "Intrcellular Domain" to -- Intracellular Domain --.

Signed and Sealed this

Sixth Day of December, 2005

JON W. DUDAS
*Director of the United States Patent and Trademark Office*